US00PP08488P

United States Patent [19]

Anderson et al.

[11] Patent Number: Plant 8,488

[45] Date of Patent: Dec. 7, 1993

[54] CANKER-RESISTANT ASPEN TREE 70-144-30-68-1

[75] Inventors: Neil A. Anderson, Roseville; Michael E. Ostry, Blaine, both of Minn.

[73] Assignee: Regents of the University of Minnesota, Minneapolis, Minn.

[21] Appl. No.: 675,502

[22] Filed: Mar. 25, 1991

[51] Int. Cl.[5] ..... A01H 5/00

[52] U.S. Cl. ..... Plt./53

[58] Field of Search ..... Plt./53

[56] References Cited

PUBLICATIONS

Anderson, N. A., et al., (1979) "Insect Wounds as Infection Sites for *Hypoxlon mammatum* on Trembling Aspen". *Phytopathology* 69:476–479.

Einspahr, D. W., et al., (1977) *Genetics of Quaking Aspen* USDA Forest Service Res. Pap. WO-25, 23 pages.

Ostry, M. E., et al., (1983) "Infection of Trembling Aspen by *Hypoxlon mammatum* through Cicada Oviposition Wounds" *Phytopathology* 73:1092–1096.

Ostray, M. E., et al., (1990) "Development of Tissue Culture Systems for Increasing the Disease Resistance of Aspen" In: *USDA FS Gen. Tech. Rep. NC*-140. 237–241.

Strothman, R. O., et al., (1957), "Silvical Characteristics of Quaking Aspen" Lakes States Stn. Pap. No. 49. 26 pages.

*Primary Examiner*—James R. Feyrer

*Attorney, Agent, or Firm*—Merchant, Gould, Smith, Edell, Welter & Schmidt

[57] ABSTRACT

An aspen tree having rapid growth, good form, aesthetic appearance, and resistance to Hypoxylon canker caused by the fungus *Hypoxylon mammatum.*

4 Drawing Sheets

STATEMENT REGARDING FEDERALLY SPONSORED RESEARCH

This invention was made with government support from a grant funded by the United States Department of Agriculture (U.S.D.A.), U.S. Forest Service, North Central Forest Experiment Station Cooperative Agreement No. 13-80-23. The government may have certain rights in the invention.

This invention is a new and distinct variety of Aspen tree of the species known botanically as *Populus tremuloides* (Michx.) The variety has been identified by the number 70-144-30-68-1.

BACKGROUND INFORMATION

The genus Populus includes various species of trembling aspen, cottonwood, big tooth aspen, balm-of-gilead, white poplar and lombardy poplar. Many aspen trees are grown as forest trees, but aspen trees are also frequently planted in windbreaks, parks, and home landscapes.

This variety of *Populus tremuloides* (Michx.) has been selected because of a combination of several desirable characteristics, including rapid growth, good tree form, aesthetic qualities, and resistance to Hypoxylon canker caused by the fungus *Hypoxylon mammatum.*

All known varieties of aspen are quite susceptible to canker disease caused by infection with the fungus *Hypoxylon mammatum.* However, the cultivar described herein has exhibited good resistance to *Hypoxylon mammatum*, with calluses forming at the margins of cankers which slow or completely stop the canker growth.

This variety was selected as a ramet from a superior aspen clone growing in an aspen stand in Block 70 of the Pike Bay Experimental Forest on the Chippewa National Forest, near Cass Lake, Cass County, Minn. Root cuttings were taken in 1965 and individual trees were planted at the Rosemount Agricultural Experiment Station, Rosemount, Minn. in 1968 and at the Oconto Seed Orchard on the Nicollet National Forest, Langlade, Wis. in 1971. The trees were planted at a spacing of 10×10 meters which enhances canker infection and provides greater selection pressure to identify resistant trees. Several times each growing season, observations have been made of these plantings of the variety with respect to growth, form, resistance to disease and resistance to insects.

The variety described herein has continued to exhibit a novel combination of characteristics, including rapid growth, good form and aesthetic appearance, and most notably a good resistance to canker disease caused by infection from the fungus *Hypoxylon mammatum.*

Asexual Propagation

This variety has been asexually or vegetatively propagated from root cuttings collected in the field, from single node explants in tissue culture, and from invitro-grown sterile root cultures. Plants have been grown from all of such methods of propagation and have been planted in the field at the Pike Bay Experimental Forest on the Chippewa National Forest, near Cass Lake, Minn., at the Rosemount Agricultural Experiment Station, Rosemount, Minn., and at the Oconto Seed Orchard on the Nicollet National Forest, Langlade, Wis.

Asexual propagation of this variety may be easily accomplished by use of root suckers, under greenhouse conditions. It has also been determined that the tree of this variety may be vegatatively propagated by tissue culture techniques, whereas most other clones of aspen trees have not yet been successfully propagated by tissue culture.

It has been determined from observation of the numerous plantings, asexually propagated from this variety, that the characteristics described herein are firmly fixed through successive generations and that the distinguishing characteristics hold true to form through succeeding propagations.

DESCRIPTION OF THE DRAWINGS

This new variety of aspen tree is illustrated by the accompanying photographic drawings, with colors therein being exhibited as nearly true as is reasonably possible with color illustrations of this character.

DESCRIPTION OF THE VARIETY

The following traits or characteristics have been repeatedly observed and are believed to be characteristics of this cultivar which, in combination, distinguish this variety of aspen tree as a new and distinct cultivar.

No references to color are included in this description since all parts of the tree apparatus to be indistinguishable in color from the species and are typical thereof.

The ploidy of this *Populus tremuloides* has been determined to be a normal diploid, by means of chromosome counts and DNA measurements using flow cytometry.

At the two above-noted plantations at the Rosemount Agricultural Experiment Station and the Oconto seed orchard, the tree of this variety was grown from asexually reproduced sprouts as clonal trees. The trees were grown at a spacing of 3 meters×3 meters. The height and diameter growth of the trees of this variety averaged 20% greater than any of the other *Populus tremuloides* selections grown at such plantations, over a period of 27 years at the Rosemount Plantation and for 22 years at the Oconto Plantation.

The tree of this variety was selected because of its superior growth rate and aesthetic appearance. This selection develops uniformly spaced, strong lateral or scaffold branches, which arise from the trunk at uniform angles, while the central leader is distinctly straighter, as compared to over 600 other clones or varieties of aspen trees. The faster growth rate and large vigorous canopy of this tree results in shading of the lower branches and thus the shedding or natural pruning of such lower branches. The result is a straight stem or trunk and a vigorous crown, which makes the tree of this variety a dominant tree when competing against other clones or varieties of aspen trees of its own age. The vigorous growth rate of the tree of this variety also makes the tree a good competitor in forest sites, as well as gardens and parks. Root suckering of the three of this variety is particularly vigorous as compared to other varieties or selections of aspen trees.

THE TREE

The variety has a form typical of aspen trees, but with a more vigorous and rapid growth than is typical of the species and other varieties of aspen trees.

In other respects, the variety is also typical of the species. The bark color; tree shape and habit; the leaf size, shape and color; buds; and flowers are not distinctive and are typical of the species, when grown in the same areas.

The parent ramet of the variety had a diameter at breast height of 55.5 cm and was 33.84 m tall at 76 years of age.

Figure 1:
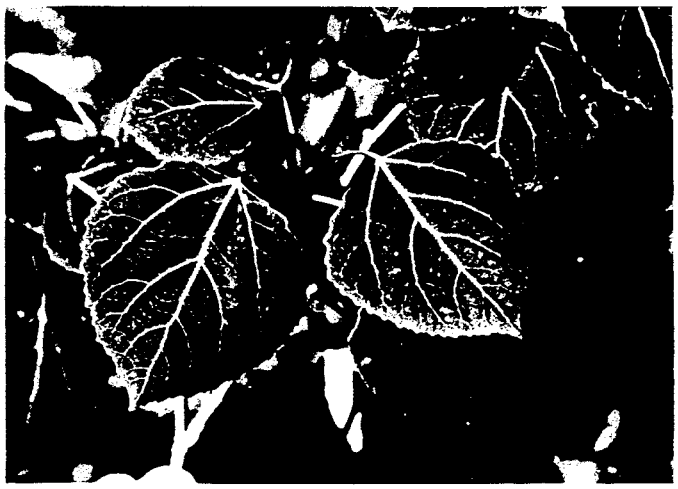
FIG. 1 is a color of photograph of a branch of a ramet of the cultivar showing typical leaves, (photo taken August of 1990, Chippewa National Forest)
Figure 2:
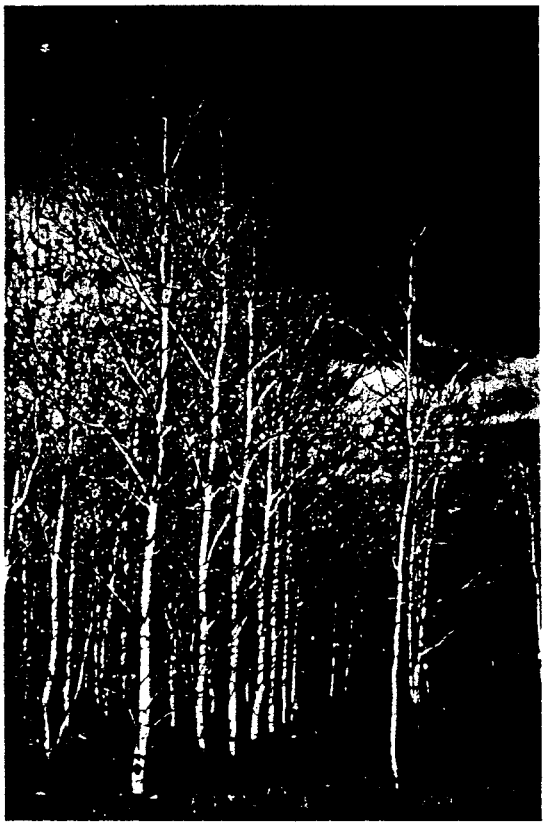
FIG. 2 is a color photograph showing this cultivar at 20 years of age and in the center row of plantings, as compared with other plantings of aspen trees of the same age, and illustrating the more vigorous growth habit of this variety, (FIG. 2 being taken in the late autumn of 1988, Rosemount, Minn.).
Figure 3:
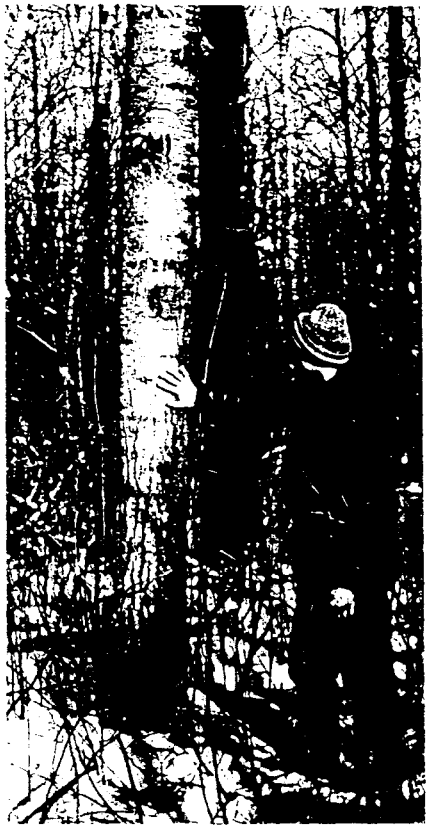
FIG. 3 is a color photograph of the trunk of a mature ramet of this variety shown in a stand of aspen in the Chippewa National Forest, Cass Lake, Minn. (photo taken in December of 1988)
Figure 4:
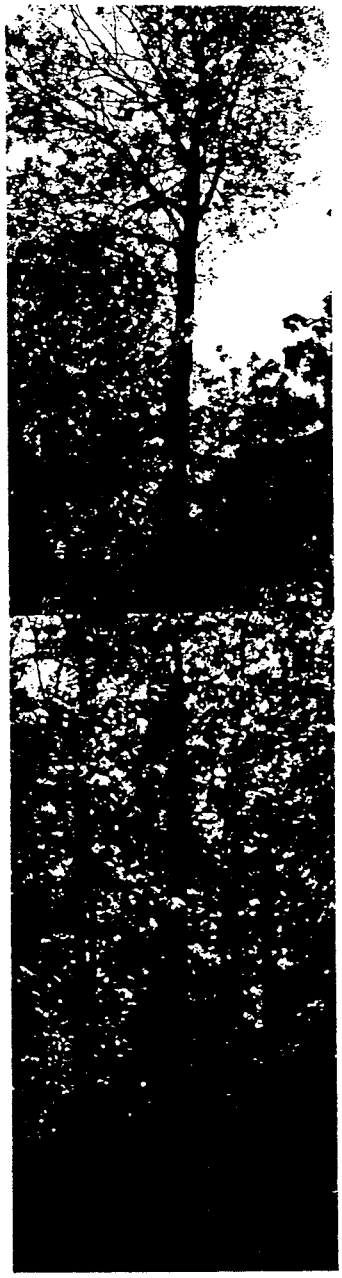
FIG. 4 is a composite photograph taken in August of 1990, and showing an individual ramet of the mature clone as photographed in the Chippewa National Forest, Cass Lake, Minn., and illustrating the mature shape and form when grown in such forest location.

Bark: The bark is smooth, gray-green on young trees, later becoming deeply fissured and gray to black on the lower portions of the trunk of older trees, as illustrated in FIGS. 2, 3 and 4. The bark color is not distinct from other members of species.

Leaf: Light green and glabrous above, duller green and glabrous below during growing season, and turning yellow in autumn.

Shape: Nearly orbicular, truncate or rarely subcordate at the base; short acuminate apex; evenly crenate-serrulate margin.

Aspect: Entirely glabrous when mature.

Size: Length from 2.5 cm to 5.0 cm; width from 2.3 cm to 5.00 cm.

Petioles: Length from 2.5 cm to 5.3 cm, approximately equal in length to the leaf blades, slender and laterally flattened.

FLOWER

The variety produces deep red staminate flowers only, in catkins 3–6 cm long, and pollen from the variety has provided vigorous progeny in crosses made over the past five years.

The tree of this variety has male flowers only, and staminate catkins appear in advance of the leaves and are 3 to 6 cm long and less than 1 cm thick. Stamens number 6 to 12 and deep red pollen sacs are born on a disk that is subtended by a 3 to 5 cleft, silky-hairy bract. Pollen from this tree has been used in a number of crosses, resulting in seedling progeny which are being evaluated in a genetic study on *Populus tremuloides*.

FRUIT

None, since the variety produces pollen only.

BUDS

Bud scales are smooth, shiny, and deep brown in color. Terminal buds are conical, sharp pointed, slightly resinous, covered by 6–7 imbricated scales.

HARDINESS

The cultivar is hardy and resistant to winter die-back.

DISEASE AND INSECT RESISTANCE

Figure 6:
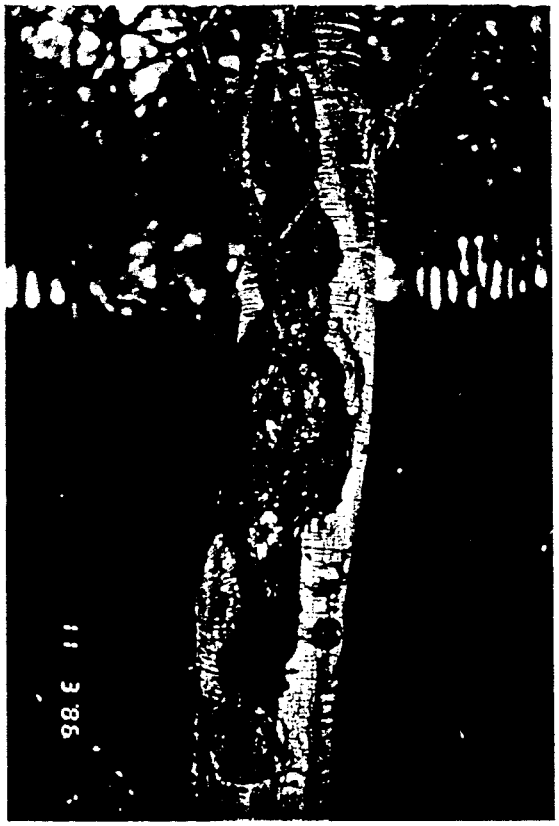
FIG. 6 is a color photograph (taken in July of 1989) of a 24 year old ramet of the variety growing in a planting of the variety at the Rosemount Agricultural Experiment Station, Rosemount, Minn. and illustrating the callus which inhibits the extension of Hypoxylon canker.
Figure 7:
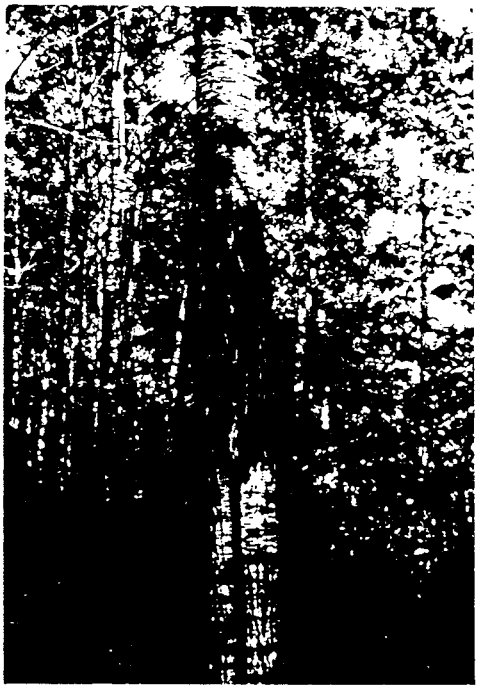
FIG. 7 is a mature ramet of the variety growing in a planting at the Chippewa National Forest, Cass Lake, Minn. and also illustrating the callus growth which has prevented further expansion of the canker (photo taken in June of 1990)
Figure 8:
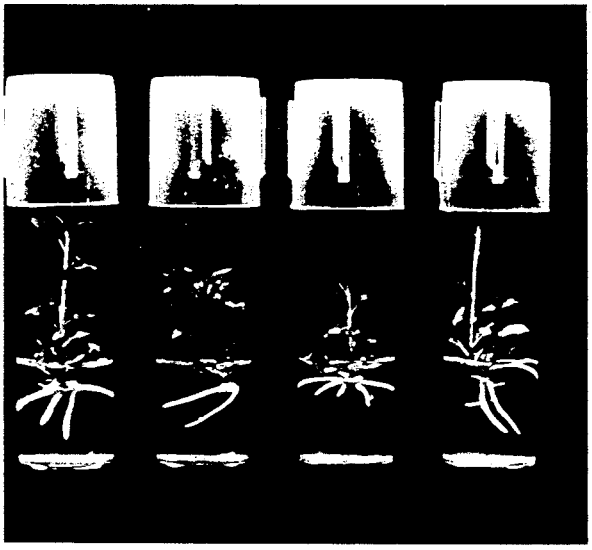
FIG. 8 is a photograph of plantlets of the variety generated by means of tissue culture (photo taken in June of 1990).

The cultivar has good resistance to *Hypoxylon mammatum*. Calluses usually form at the margins of the cankers and slow or completely stop canker growths, as illustrated in FIGS. 6 and 7. All known varieties of aspen trees are very susceptible to infection by such fungus. However, this variety exhibits more resistance to *Hypoxylon mammatum* by developing the noted calluses which slow or completely stop the canker growths. In a 20-year test at Rosemount, Minn. the other 574 aspen in the experiment averaged 2.9 cankers per tree. Members of this clone averaged 1.8 cankers per tree and callus tissue on the margins of these cankers slowed canker growth.

In the juvenile stage, the cultivar is susceptible to powdery mildew caused by *Uncinula salicis* and shoot blight caused by *Venturia macularis*.

Figure 5:
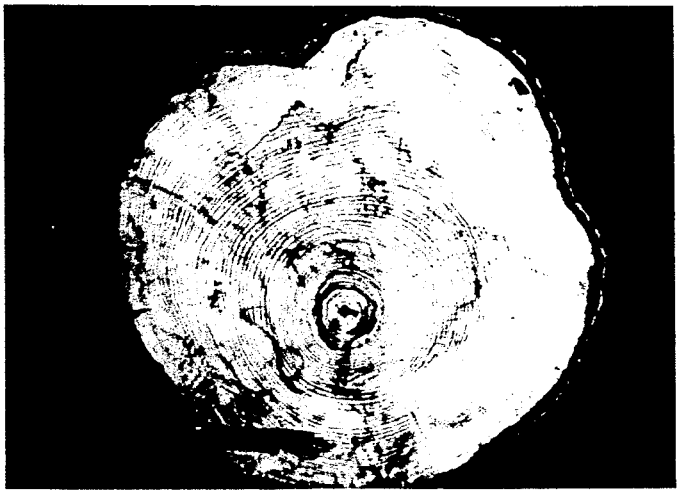
FIG. 5 shows a cross-section of a mature ramet of the cultivar, illustrating the sound wood at 76 years of age.

A cutting of the parent ramet at 76 years of age produced a diameter of 55.5 cm at breast height, and there was little white trunk decay caused by the fungus *Phellinus tremulae*, as noted in FIG. 5.

Insect Resistance

The cultivar has good resistance to wounding insects by rapidly forming callus tissue to seal the wound.

WOOD

Wood produced by the tree of this variety is of high quality and generally free of stain and decay, as compared to wood from other known varieties of aspen trees. The rapid growth rate and natural pruning habit with respect to the lower branches produces wood which is generally free of knots, as compared to other known varieties of aspen trees. The ability of this tree to form callus tissue in response to wounds limits the amount of stain and decay fungi that enter the tree. The result is wood which is generally clean and of high quality, compared to the wood from most other known varieties of aspen trees. It is therefore believed that the wood from trees of this variety will be in demand for pulp and fiber use.

We claim:

1. A new and distinct variety of aspen tree, substantially as shown and described herein, characterized particularly as to novelty by rapid growth, good form, aesthetic appearance, and resistance to Hypoxylon canker.

* * * * *

UNITED STATES PATENT AND TRADEMARK OFFICE

CERTIFICATE OF CORRECTION

PATENT NO. : Plant 8,488

DATED : December 7, 1993

INVENTOR(S) : Neil A. Anderson, et al.

It is certified that error appears in the above-identified patent and that said Letters Patent is hereby corrected as shown below:

On the title page, at Assignee [73], after "Regents of the University of Minnesota, Minneapolis, Minn." insert --U.S. Department of Agriculture-Agricultural Research Service, Beltsville, MD--.

Signed and Sealed this

Sixth Day of December, 1994

*Attest:*

Bruce Lehman

BRUCE LEHMAN

*Attesting Officer*

*Commissioner of Patents and Trademarks*